United States Patent [19]

Renner

[11] 4,262,306
[45] Apr. 14, 1981

[54] METHOD AND APPARATUS FOR MONITORING OF POSITIONS OF PATIENTS AND/OR RADIATION UNITS

[76] Inventor: Karlheinz Renner, Am Wäldchen 15, 3000 Hannover-Isernhagen, Fed. Rep. of Germany

[21] Appl. No.: 96,479

[22] Filed: Nov. 21, 1979

Related U.S. Application Data

[63] Continuation of Ser. No. 898,521, Apr. 20, 1978, abandoned.

[30] Foreign Application Priority Data

Apr. 27, 1977 [DE] Fed. Rep. of Germany ....... 2718804

[51] Int. Cl.³ .............................................. H06N 7/18
[52] U.S. Cl. ..................................... 358/93; 358/101; 358/103; 358/105; 358/106; 358/107; 358/108; 358/111; 128/303 B
[58] Field of Search ................. 358/93, 101, 103, 105, 358/106, 107, 108, 111; 128/303 B

[56] References Cited

U.S. PATENT DOCUMENTS

| 3,283,071 | 11/1966 | Rose | 358/93 |
|---|---|---|---|
| 3,567,853 | 3/1971 | Green | 358/93 |
| 3,673,317 | 6/1972 | Newell | 358/93 |
| 4,058,114 | 11/1971 | Soldner | 128/303 B |
| 4,118,730 | 10/1978 | Lemelson | 358/93 |

FOREIGN PATENT DOCUMENTS

| 1766346 | 7/1971 | Fed. Rep. of Germany . |
|---|---|---|
| 2158535 | 6/1972 | Fed. Rep. of Germany . |
| 2158457 | 5/1973 | Fed. Rep. of Germany . |
| 2420402 | 11/1974 | Fed. Rep. of Germany . |
| 2335923 | 1/1975 | Fed. Rep. of Germany . |
| 2361155 | 6/1975 | Fed. Rep. of Germany . |
| 1265933 | 3/1972 | United Kingdom . |
| 1328355 | 8/1973 | United Kingdom . |
| 1479406 | 7/1977 | United Kingdom . |
| 1489678 | 10/1977 | United Kingdom . |

*Primary Examiner*—Howard W. Britton
*Attorney, Agent, or Firm*—Cushman, Darby & Cushman

[57] ABSTRACT

An account is given of a method for monitoring of the position of patients and/or radiation units in which a first position is taken by a camera and stored and comparison between the stored position and the second position taken by the camera takes place. The first position taken by the camera and able to be reproduced as a positive or negative image is changed into a negative image and is so put into line with the second position, taken by the camera, in the positive or negative image that all image points of the first position are able to be seen in a first color contrast and that all image points of the second position are able to be seen in a second color contrast and in that all image points which are in line are able to be seen in a third color contrast. The second position of the patient and/or of the radiation unit is changed till only the third color contrast is to be seen.

37 Claims, 3 Drawing Figures

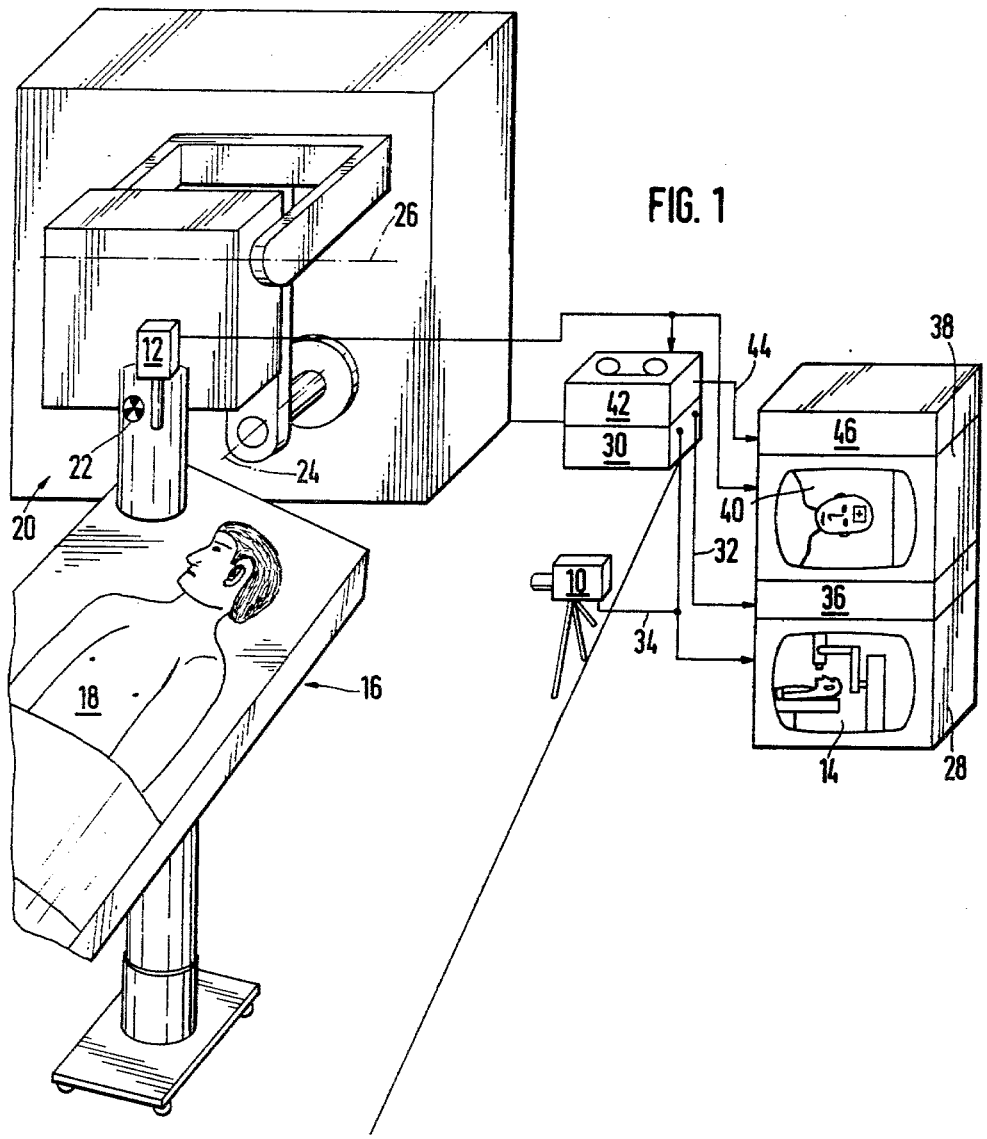

METHOD AND APPARATUS FOR MONITORING OF POSITIONS OF PATIENTS AND/OR RADIATION UNITS

This is a continuation of application Ser. No. 898,521, filed Apr. 20, 1978, abandoned upon the filing hereof.

BACKGROUND OF THE INVENTION (1) Field to which the invention relates

The invention relates to a method for monitoring the position of patients and/or radiation units in which a first position is taken by a camera and stored and comparison between the stored position and the second position taken by the camera takes place.

(2) The prior art

An account of such a method and an apparatus for it is given for example in the German specification (Offenlegungsschrift) No. 2,335,923. In this case scales are placed in and around the head zone of a patient for making radiological pictures. With the help of these scales and a comparison photograph position monitoring is then possible on taking in a second position.

This makes it clear that in medicine there is a great need for making it possible for the body or part of the body of a patient to be put as accurately as possible into a position which is the same as the original position, for new treatment. The more danger there is with the radiation used on the patient, the more important it is for the earlier and the later position to be the same to the greatest possible degree. So for example using radiation on a tumor it is most important that only the tumor itself and not the healthy tissue near it is put under the effect of the radiation.

So the German specification (Offenlegungsschrift) No. 2,158,457 gives an account of a positioning system for patients having the purpose of putting the patient in the same position a number of times. On the support face of the positioning system, on which the pelvis and top leg parts of the patient are to be supported, pressure and force measuring parts are placed, whose readings are used for positioning the patient at any time in the same way, that is to say in the same position. It will however be readily seen that more particularly in the case of patients, that is to say persons having a disease, great changes in weight are likely. So at the small number of points, at which the pressure and force measuring parts are used, incomplete accuracy is likely. So for example in the German specification (Offenlegungsschrift) No. 2,420,402 there is a suggestion for positioning the patient by using plastics supports, which have in them a substance, whose foaming and rapid hardening is caused. This method as well has the shortcoming that even a small loss of weight of a patient makes a space between the fitting form of the plastics support and the patient himself so that once again it is not possible to make certain that the patient will have the same position as earlier. Furthermore in addition to the complex, highly-priced and time-taking construction of a half body-shell, a great amount of space is needed, in which the body-shells are kept, from which it is possible to take them as quickly as possible for use.

Furthermore the German specification (Offenlegungsschrift) No. 2,361,155 has a system and a method for fixing and keeping a position-relation between two structures. In this respect a patient is to be put in a certain position in relation to a radiation unit and to be kept exactly in the position taken. For this purpose there is the suggestion of using a light unit with the radiation unit for producing a light ray of concentrically patterned light with an intensity changing from the middle point to the outside parts. Furthermore there is a reflecting target on the patient for reflecting the light ray of concentrically patterned light. There is also a light feeler, which is acted upon by the light reflected at the target and is so placed that a signal is produced, which is proportional to this light intensity. Furthermore a control part is used for making out the position-relation between the first and the second structure, that is to say the radiation unit and the patient. This control part is for controlling the movement of the support face for the patient. With this method and this apparatus it is for this reason only possible for the support surface, to be positioned dependent on the motion of the patient in treatment, to be in line with each movement of the patient. The outcome is that there is no undesired action of radiation at any time and wrong radiation of healthy body parts is decreased.

Furthermore however the radiation unit is to be able to be so placed that its movement is the same as that movement, used in the first treatment. This is to say that the movement of the radiation source is to be able to take place as accurately as possible along the lines of each treatment of a patient. For this purpose the German specification (Offenlegungsschrift) No. 1,766,346 has already given an account of an apparatus for the automatic adjustment of a radiation unit, in which the use of a data input makes possible regulation of the movement of the radiation unit to be the same as an earlier adjustment or movement. It is clear that such an apparatus, in addition to the most different sorts of measuring feelers and servo-motors, makes necessary a complex system for getting data and for its input and with which a movement, which has been caused to take place once, of the radiation unit can be caused to take place again.

SHORT ACCOUNT OF THE INVENTION

On the other hand one aim of the invention is that of making possible a method and an apparatus of the sort made out with which using very simple normal parts any desired position, be it of a patient or be it the position of a radiation unit is able to be taken up again with a very small, if any, error. Further developments of the invention of good effect are given in the dependent claims.

One particularly good effect of the teaching of the invention is that the method and apparatus for it are able to be used with normal radiation apparatus, since the method and its apparatus are not limited to any particular construction of a radiation apparatus, because a camera fixed in space is able to be placed nearly anywhere near the radiation unit and normally the placing of a camera joined to the radiation unit is possible in the ray path or at least near it.

Lastly a very important effect of the present invention is that even markings on the skin of the patient, which are normally thought of as troublesome, are no longer needed, because the great number of different picture points and more particularly readily seen contour lines make such markings unnecessary.

Furthermore the first position of the patient and of the radiation unit can be stored, for example on a magnetic tape on a patient record card, so that in this way, or by using a long-tape storage system, very little time is needed to get at the record when the next treatment takes place.

Furthermore a new position taken up is able to be monitored all the time with the apparatus and method of the invention, since the person using the apparatus is able to see any changes in position on his monitor all the time and give a note of them to the patient in the treatment room through an intercommunication and say that the patient is to make a change in the position of his body.

LIST OF VIEWS OF THE DRAWINGS

An account of one form of the invention will now be given with reference to the accompanying drawings.

FIG. 1 shows in perspective how the different units as for example the camera fixed in space and the camera fixed in relation to the radiation source are placed and how they work together.

FIG. 2 is a view of the positions taken with the camera fixed in relation to the radiation source, with three color contrasts making it clear that there is an error in the distance with respect to the radiation source.

FIG. 3 is a view of positions taken with the camera fixed in space using the three color contrasts making it clear that the patient has to make a nodding motion with his head in order to make good the error in position and that there is a position error because the radiation source does not have the same adjustment as originally.

DETAILED DESCRIPTION OF THE INVENTION

In FIG. 1 the apparatus of the invention has a camera 10 fixed in space and a camera 12 fixed in relation to the radiation unit. For the method of the invention the camera 10 is generally enough, if it is so placed in the radiation room that an image 14 from the space-fixed camera 10 has in it a radiation table 16 with the patient 18 on it and as well a radiation system 20 for use with the table 16.

On the first treatment the radiation for the patient 18 in question is worked out in respect of intensity and direction and the outcome is used for adjustment of the radiation system 20, that is to say there is either to be a fixed adjustment of a radiation unit 22 or in a certain direction of movement firstly in relation to the radiation table 16 and then to the patient 18. The radiation unit 22 is able to be turned about an axis 24, running in the length direction of the radiation table 16 and, for this reason, of the patient 18, or parallel to them. Furthermore the radiation unit 22 is then to be turned about an axis 26 running at right angles to the axis 24. Lastly the radiation unit 22 can be changed in position in the direction of the axis 24 so that in the range of movement of the radiation unit every space-coordinate on the radiation table can be put under radiation.

So on the first radiation treatment of a patient 18 the given position or the given movement of the radiation unit 22 is taken with the space-fixed camera 10 and then reproduced as the picture or image 14 or as "film" by a first TV monitor 28. At the same time each image or picture taken by the space-fixed camera 10 is broken down into separate image points along a number of lines. These image points are digitalised in line with their color-contrast value and encoded binarily or tertiarily. The encoded image points are stored, on the lines of their separate digital value and their order, in a memory 30. It is possible for the memory 30 to be a magnetic tape memory, a magnetic core memory, a semiconductor memory or the like. It is within the invention to put digitalised values or data on a card on the patient filing index, the data being for instance in a punched tape or the like on the card, so that direct access is possible in the order of treatment of different patients. Furthermore it is within the invention to have storage in a central computer of the hospital using a data line joined to it.

In the treatment with radiation coming after the first treatment coarse adjustment is possible using the stored, original position. For this purpose the stored position is put on the TV monitor 28. It is however as well for the stored position to be sent to the TV monitor 28 through an inverter line 32 so that it is not the positive image of the originally stored position but the negative image which is to be seen, that is to say the first color contrast, for example a dark color contrast is changed into a second color contrast, that is to say a bright color contrast. If the space-fixed camera 10 is now turned on and the image made by it of the second or following position is also put on the TV monitor 28, the image points coming from the monitor 28 will be seen in a positive view, that is to say all image points, which are in fact dark, will be seen on the TV monitor as such and are therefore in line with the first color contrast. This putting together of the image coming through the inverter line 32 and the image coming through a camera line 34 is made possible by an addition circuit 36. The addition circuit 36 is for this purpose to be so designed that there is addition of the separate image points with the right values and positions. In place of an inverter line and an addition circuit it is possible to make use of a subtraction circuit as well. The inverter line 32 and the addition circuit 36 or a subtraction circuit are able to be integrated in the TV monitor 28 as well.

If the position taken originally by the camera 10 and stored in the memory 30 is the same as the second or a later position, which is taken by the space-fixed camera 10, the image on the TV monitor 28 will have a third color contrast, which comes between the first and the second color contrasts.

If for example the first color contrast is black and the second one white, the third color contrast will be a grey value. The purpose and effect of the separate color contrasts will be seen by the later account having to do with FIGS. 2 and 3.

It is possible for the space-fixed camera 10 to be used for position monitoring of the radiation system and of the patient 18 as well. It is to be noted that by using the relation between the first and the second color contrast and specially the contour lines going round the color contrast it is possible not only to see, and so put right, a difference in position in the image plane but also deep in the image.

This will be seen specially clearly on looking at the image in FIG. 2, which has been taken by the camera 12 fixed in relation to the radiation unit and which is placed in the ray path or near the ray path of the radiation unit and so sends the image 40 to a TV monitor 38, the image 40 bringing at least generally the same as the radiation field of the radiation unit 22. As made clear earlier the camera 12 fixed in relation to the radiation unit, is not necessary in all cases for the method noted earlier. However the camera 12, fixed in relation to the unit, is of good effect as a further position check, because the radiation field can be still more accurately monitored with respect to the position being the same, because of the smaller distance. Furthermore there is a different view point or perspective, from which the distance and twist errors are able to be seen even more accurately. The camera 12 fixed in relation to the radiation unit is able in this case to be joined with the same TV monitor 28 as the space-fixed camera 10 or with the separate TV monitor 38. Furthermore the memory 30 put in for the space-fixed camera 10 is able to be made greater in size by having a further memory 42 for the camera 12 fixed in relation to the radiation source.

This goes as well for a separate inverter line 44 and addition circuit 46. It is naturally possible for the memory 42 of the camera fixed in relation to the radiation unit, and the TV monitor 38 connected with it for the inverter line 44 and addition circuit 46 to have their place taken by a subtraction circuit. In this case I have a parallel system of completely the same design for the space-fixed camera 10 and the camera 12 fixed in relation to the radiation unit.

For these two cameras 10 and 12 it is in particular possible to have TV cameras of a normal design. However as part of the invention with a simpler form it is possible to make use of photographic cameras whose separate images make for the three different color contrasts in a like manner. It is for example possible to use moving picture cameras as well. In this case the first position is taken and so recorded. The second or the next position is then able to be produced for example using light amplification through a fixed objective, to which the film camera was joined for the first position. The projection through this fixed objective and the recorded film are then able to be further processed or used in the method of the invention. Lastly it is possible to use infrared or other cameras as well, which have the property of taking pictures in a certain, desired wavelength range.

Furthermore there is much to be said for the use of X-ray cameras, that is to say cameras changing X-rays acting on the body of the patient in only a slight amount, that is to say in a low dose, into an image or picture, because in this case it is possible to see for example even during radiation if the position and therefore the size and position of a tumor or of any other part of the body which is interesting has been changed.

In FIG. 2 it is possible to see the first and second position taken by the camera 12 fixed in relation to the radiation unit, in use of the method of the invention. The outer contour (full lines) is for the first position and the inner contour (in broken lines) is for the second position. Owing to the even parallel changing in position of the contour lines in the image plane it is at once to be seen that there is a distance error between the two positions. The outcome of this is that a height adjustment of the radiation table is necessary so that the patient comes nearer to the radiation source, this movement going on till the two outlines are in agreement. If however the body has for example even a grey shade, this being for the third color contrast, it will only be necessary for the head of the patient to be moved upwards, that is to say the head has to be somewhat nearer to the radiation unit. This quick discovery of the distance error is made possible for example by comparison of two positive or negative images or pictures, since it is only the difference to be seen more strongly of the two outlines which makes the error clear. The outcome is that a great redundance of image points makes a third dimension clear on the picture screen. So the main point of the invention is that separate image points, which are not able to be seen as connected with an error by the human eye, are only to be seen on integration. The outcome of this integration is that a large number of image points, which make it possible to see errors, are put together by this method for the right purpose.

FIG. 3 is the image of the space-fixed camera 10, the scale being greater than in image 14. The image is again of the head of the patient 18. It is to be seen that with a first outline (a full line) the first position is not in agreement with the second position with respect to the second outline (in broken lines). This goes as well for a part, still to be seen in the image, of the radiation system 20. This picture firstly says that the radiation system 20 has not yet had the right adjustment, that is to say it has not been given the radiation adjustment as used in the first radiation treatment. When I have the right adjustment of the radiation system, something to be seen by agreement of the outlines for example, the head of the patient is able to be put in the right position as well. In this case the outcome is that the patient has to make a small nodding movement in a downward direction, that is to say towards the chest. Speaking to the patient for this purpose is for example through an intercommunication system in the treatment room. If for example the outline of the ear is changed in position in parallelism, the head of the patient will have to be turned somewhat until this outline is in agreement with the original one, that is to say no first and second color contrasts are to be seen any longer and on the image or picture only a third color contrast as for example a grey shade is to be seen.

The images of FIGS. 2 and 3 are limited as regards the information in them, because the image is limited to outlines. The method of the invention will however be very much clearer when full images or pictures of a patient or of a radiation system make clear the good points of the invention, for it is only then that the great redundance of the separate image points with the great amount of information in them makes itself clear. This amount of image points, put together with a well-reasoned system, with different color contrast values is then able to be of full effect, that is to say that the orders to the patient for changing the parts of his body not yet in the right position, are able to be made clear to the patient by any normal person, that is to say not an expert. In an interesting further development of the invention use is made of color cameras so that for example the first color contrasts and the second color contrasts come into view as complementary colors on the image screen or the like.

So it is possible to say that the apparatus of the invention, which is generally made up using parts that are readily come by, is able to be used for all radiation rooms without being dependent on their technical state, because in every case a well-planned development is made possible. With the method of the invention very much more accurate radiation is possible because the positions to be used by the patient are generally the same and this accuracy is made possible if only a person without experience is used for checking at the picture screen and gives the orders to the patient in the treatment room.

Naturally the method of the invention is to be used not only for radiation systems but generally for all moving objects as well, having to be noted that both the system which is fixed in relation to the radiation unit and also the space-fixed system is able to be used independently of the other. The wording "fixed in relation to the radiation unit" is used in this respect generally for camera observation going from a moved object.

As an example a system with a ship, aircraft, motorcar or any other system may come into question, in which relative movements between a fixed position and a moved position are to be monitored and recorded. With the method of the invention it is possible as well for an O-point, which is generally the same as the space-fixed position, to be placed on a moving object. This is for example likely to be the case when the position monitoring is from a ship, in the case of which the relative movement and for this reason the position change between the viewing ship and the coast or harbour line and an other ship is to be viewed or recorded. If for example from the viewing ship the movement of an other ship is to be seen from the view point of an other ship as well, in this case the relative movement of the two ships towards and away from each other would be made clear, but a very much better and, for this reason, more informative discovery of the position would be possible only however if for example from a lighthouse camera monitoring information is sent to the viewing ship, the lighthouse being at right angles to the connection line between the two ships at a certain distance at the coast. Uses of the same sort are for example for the monitoring of other transport systems as well or for monitoring an object as for example a house, which is to be safeguarded.

Since in the method of which an account has been given above it has been taken as well that cameras are used making pictures with wavelengths dependent on the desired purpose it is for this reason possible as well, for example for safeguarding a house, not only to take into account changes in the visible wavelength range but in other wavelength ranges as well, as for example in the infrared wavelength range. The outcome would be for example that the camera takes, for example, difference pictures when an intruder is getting over a fence, since in this case the earlier position of the fence will be different to the position for which the fence and the intruder are to be seen. So the third color contrast will make clear those parts of the fence, which are the same as the earlier position of the fence, while changes in the fence will be seen in the form of the intruder in the first or second color contrast and, for this reason, very much better information is put to hand. A further camera would be able, for example to make clear thermal changes, as for example the breaking out of a fire. Furthermore pressure waves could be pictured in this way, in which case again only those changes are to be pictured, which are different to the earlier stored picture. This list of examples of the invention may be gone on with, though however the present application has to be kept within certain limits and every expert on being given knowledge of the invention is able to come across these and other uses on his own.

An important point with the invention is for this reason to be seen in the use of a two-dimensional or sheet image with very many points as a factor of calculation and the image points, which are the same as an earlier two-dimensional image are of a less interest, while, more importantly, the difference in the image points is used for further processing of the information in the form of the difference image points. So, putting the question in very simple wording, it is a question of a calculator or computer with an optic memory, in which firstly those optical memory values are taken into account, which have been changed with respect to optical values stored earlier and in the case of which it is only then that the processing of that information or data is started, which has been filtered out in the foregoing system at different values. This putting in beforehand and later is naturally able to be joined together and mixed as is desired.

What I claim is:

1. A method for adjusting a second position of a patient and/or a radiation unit to coincide with a previous first position of the patient and/or radiation unit comprising the steps of:
    generating by the use of a camera during a first interval of time first position data related to a first position of a patient and/or a radiation unit;
    storing the first position data in a data store;
    generating by the use of a camera beginning at a second point in time subsequent to the end of the first time interval, second position data related to a second position of the patient and/or radiation unit;
    retrieving the first position data from the data store;
    displaying a first image related thereto;
    displaying simultaneously with the displaying of the first image, a second image related to the second position data;
    comparing the displayed images;
    adjusting the second position of the patient and/or or radiation unit so as to minimize the difference between the first and second images; and
    repeating said steps of comparing and adjusting as often as necessary to produce alignment of the first and second images, whereby the second position of the patient and/or radiation unit will be substantially the same as the first position of the patient and/or radiation unit.

2. A method according to claim 1 wherein said step of displaying a first image related thereto includes a step of displaying a first image in a first color contrast.

3. A method according to claim 1 wherein said step of displaying simultaneously includes a step of displaying a second image in a second color contrast.

4. A method according to claim 1 wherein said steps of retrieving, displaying a first image, and displaying simultaneously include the steps of:
    displaying a first image related to the first position data in a first color contrast;
    displaying a second image related to the second position data in a second color contrast; and
    displaying the overlapping portions of the first and second images in a third color contrast.

5. A method according to claim 1 wherein said step of retrieving the first position data includes the step of inverting the first image (postitive to negative or negative to positive) before displaying it.

6. A method according to any of claims 1-5 wherein during said steps of displaying simultaneously, comparing and adjusting, a parallel difference in position of the first image with respect to the second image in a plane at right angles to the picture taken directions of the camera and in a direction at right angles to the longitudinal axis of the patient and/or the radiation unit indicates a relative turning of the patient and/or of the radiation unit about its longitudinal axis between the first and second positions.

7. A method according to any of claims 1-5 wherein during said steps of displaying simultaneously, comparing and adjusting, an angle-like run of the first image to the second image in a plane at right angles to the picture taken direction of the camera indicates a relative turning of the patient and/or of the radiation unit about an axis parallel to the picture taking direction of the camera between the first and second positions.

8. A method according to any of claims 1-5 wherein during said steps of displaying simultaneously, comparing and adjusting, a parallel difference in position of the first image in relation to the second image in a plane and direction at right angles to the picture taking direction of the camera indicates a relative change in distance between the camera and the patient and/or the radiation unit in the second position with respect to the distance between the camera and the patient and/or radiation unit in the first position.

9. A method according to any of claims 1-5 wherein said steps of generating includes a step of generating by the use of a space-fixed camera during a first interval of time first position data related to a first position of a patient and/or a radiation unit.

10. A method according to any of claims 1-5 wherein said second generating steps includes a step of generating by the use of a space-fixed camera beginning at a second point in time subsequent to the end of the first time interval, second position data related to a second position of the patient and/or radiation unit.

11. A method according to any of claims 1-5 further including a step of placing guide markings on the patient and/or the radiation unit.

12. A method according to any of claims 1-5 wherein said second step of generating includes generating data obtained from a photographic camera which is space-fixed or fixed in relation to the radiation unit.

13. A method according to any of claims 1-5 wherein said first step of generating includes a step of generating by the use of a film camera during a first interval of time first position data related to a first position of a patient and/or a radiation unit.

14. A method according to any of claims 1-5 wherein said second step of generating includes generating data obtained from a TV camera fixed in position with respect to the radiation unit.

15. A method according to any of claims 1-5 wherein during each step, the position data corresponds to discrete points of its associated image and the image points are assigned a digital value representing their respective color contrast.

16. A method according to any of claims 1-5 wherein said first and second steps of generating include steps of generating digital value data.

17. A method according to any of claims 1-5 wherein said steps of displaying includes steps of displaying on a TV monitor.

18. A method according to any of claims 1-5 wherein said steps of storing includes storing on a magnetic recording unit or on a video record or in a core memory or in a semiconductor memory.

19. A method according to any of claims 1-5 wherein during each step, the position data corresponds to discrete points of its associated image and each image point is broken down into the three basic colors of a normal TV system and the color contrast of each basic color is given a digital value.

20. A method according to any of claims 1-5 wherein said second step of generating includes a step of generating by the use of a second camera that is spatially separate from a first camera for generating the first position data, beginning a second point in time subsequent to the end of the first time interval, second position data related to a second position of the patient and/or radiation unit.

21. A method according to any of claims 1-5 wherein said steps of displaying and displaying simultaneously include steps of counting the number of image points associated with each image.

22. A method according to any of claims 1-5 wherein said steps of comparing includes comparing by the use of an optical system for comparison of the light intensities of various image points of the first and second images.

23. A method according to any of claims 1-5 wherein said step of comparing includes a step of comparing by the use of electric and/or thermal light sensors to compare various image points of the first and second images.

24. A method according to any of claims 1-5 wherein said steps of displaying and displaying simultaneously includes steps of displaying various brightness stages of the images.

25. Apparatus for the position monitoring of a patient and/or a radiation unit comprising:
at least one camera for generating (a) a first position image of the patient and/or radiation unit at a first time and (b) a second position image of the patient and/or radiation unit at a second time subsequent to said first time;
means for storing the first position image;
means, coupled to said storing means and to said at least one camera, for combining the first image and the second image;
means for displaying the combined images simultaneously.

26. An apparatus according to claim 25 including at least two cameras, one of which is spatially fixed.

27. Apparatus according to claim 25 wherein said camera is a TV camera.

28. Apparatus according to claim 26 wherein said spatially-fixed camera is a TV camera.

29. Apparatus according to either of claims 27 or 28 wherein said camera operates within at least one of a plurality of wavelength ranges.

30. Apparatus according to claim 25 wherein said means for combining is an addition circuit.

31. Apparatus according to claim 25 wherein said means for combining is a subtraction circuit.

32. Apparatus according to claim 25 further including means for inverting (positive to negative or negative to positive) the image stored in said means for storing.

33. A method for monitoring the position of a patient and/or a radiation unit comprising:
generating by the use of at least one camera (a) a first position image of the patient and/or radiation unit at a first time and (b) a second position image of the patient and/or radiation unit at a second time subsequent to said first time;
storing the first position image;
combining the stored first image and the second image; and
displaying the combined images simultaneously.

34. A method according to claim 33 wherein said step of generating includes generating a first position image by the use of a first camera and a second position image by the use of a second camera.

35. A method according to either of claims 33 or 34 wherein said step of combining includes the step of adding the first and second images together.

36. A method according to either of claims 33 or 34 wherein said step of combining includes the step of substracting one of the images from the other.

37. A method according to either of claims 33 or 34 further including the step of inverting the stored first position image.

* * * * *